United States Patent [19]

Agee et al.

[11] Patent Number: 4,963,147
[45] Date of Patent: Oct. 16, 1990

[54] SURGICAL INSTRUMENT

[75] Inventors: John M. Agee, 3980 Bartley Dr., Sacramento, Calif. 95822; Francis King, Shingle Springs, Calif.

[73] Assignee: John M. Agee, Sacramento, Calif.

[21] Appl. No.: 380,624

[22] Filed: Jul. 14, 1989

Related U.S. Application Data

[63] Continuation of Ser. No. 98,610, Sep. 18, 1987, abandoned.

[51] Int. Cl.5 ............................................. A61B 17/32
[52] U.S. Cl. .................................................... 606/170
[58] Field of Search ................... 128/303.15, 305, 898; 606/159, 170; 604/22

[56] References Cited

U.S. PATENT DOCUMENTS

| 3,900,002 | 8/1975 | Widran . |
| 4,137,920 | 2/1979 | Bonnet . |
| 4,200,111 | 4/1980 | Harris . |
| 4,201,213 | 5/1980 | Townsend . |
| 4,258,716 | 3/1981 | Sutherland . |
| 4,275,735 | 6/1981 | Chutter . |
| 4,423,727 | 1/1984 | Widran et al. . |
| 4,461,280 | 7/1984 | Baumgartner . |
| 4,474,174 | 10/1984 | Petruzzi . |
| 4,499,899 | 2/1985 | Lyons, III . |
| 4,522,206 | 6/1985 | Whipple et al. . |
| 4,539,976 | 9/1985 | Sharpe . |
| 4,580,563 | 4/1986 | Gross . |
| 4,603,694 | 8/1986 | Wheeler . |
| 4,620,547 | 11/1986 | Boebel . |
| 4,633,860 | 1/1987 | Korth et al. . |
| 4,726,370 | 2/1988 | Karasawa . |
| 4,819,620 | 4/1989 | Okutsu . |
| 4,850,342 | 7/1989 | Hashiguchi . |

FOREIGN PATENT DOCUMENTS

| 2903471 | 2/1979 | Fed. Rep. of Germany . |
| 2737014 | 3/1979 | Fed. Rep. of Germany . |
| 2748057 | 5/1979 | Fed. Rep. of Germany . |
| 3408243 | 9/1985 | Fed. Rep. of Germany . |

OTHER PUBLICATIONS

Paine, Kenneth W. E., M.D. et al., "Carpal Tunnel Syndrome", J. Neurosurg., 59:1031-1036, (1983).
Ruggles Corporation, "Neurosurgical Instruments", Bulletin No. 795415, 5 pages.

Primary Examiner—Michael H. Thaler
Attorney, Agent, or Firm—Dean P. Edmundson

[57] ABSTRACT

Disclosed is an improved surgical method for inspecting and manipulating selected tissue in a body cavity, while minimizing the risk of injury to surrounding tissue, and a surgical instrument therefor.

23 Claims, 5 Drawing Sheets

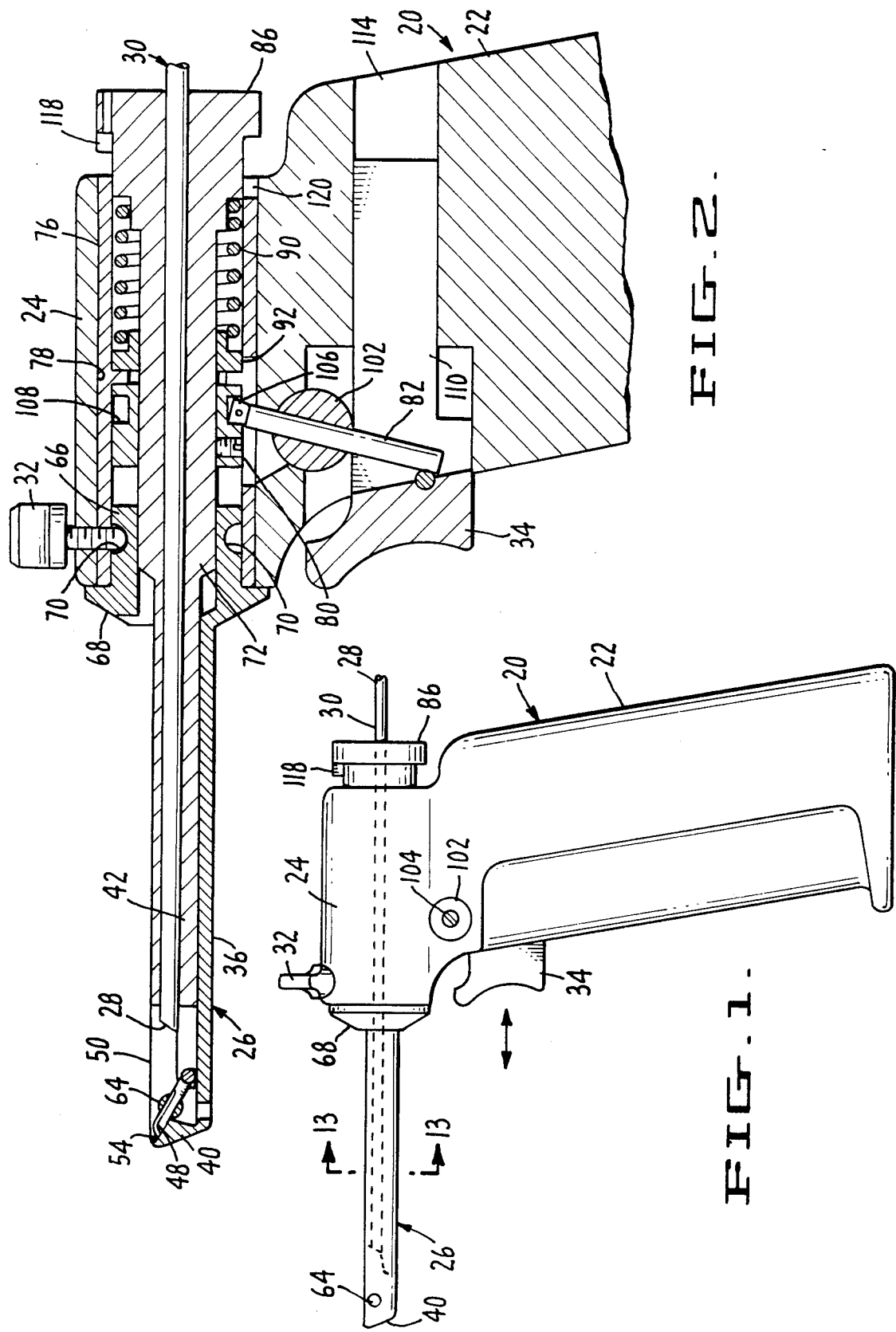

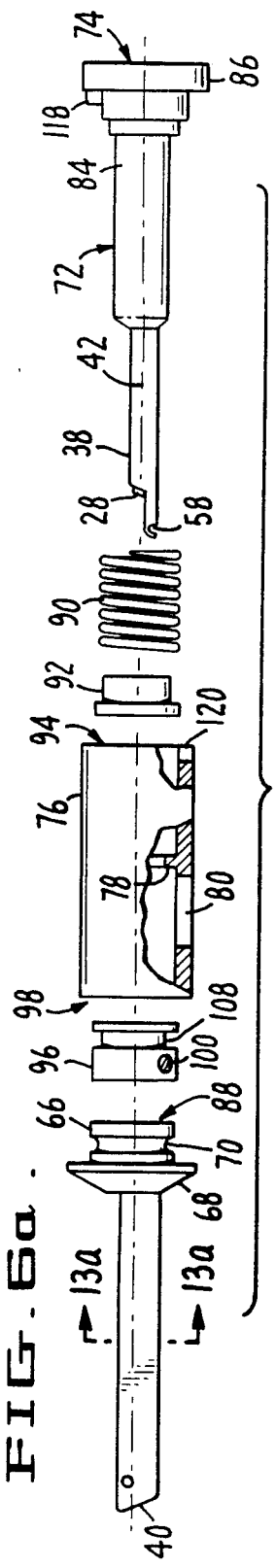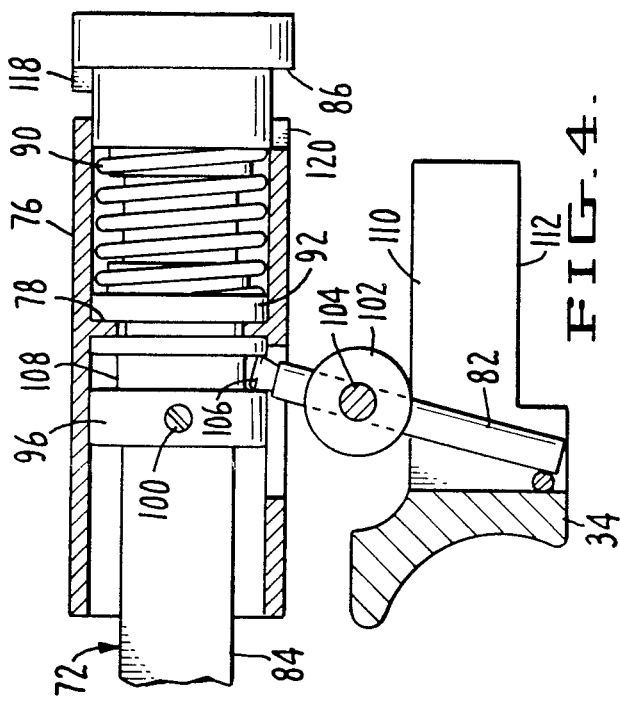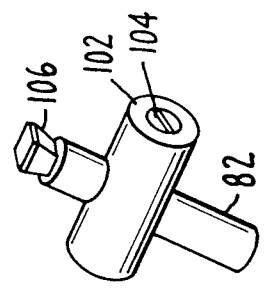

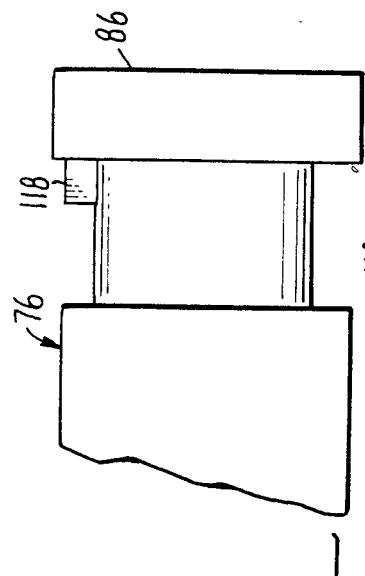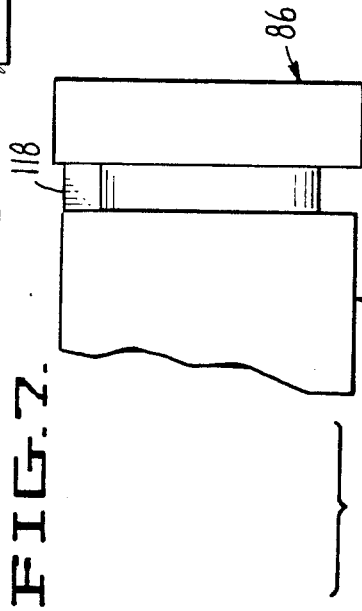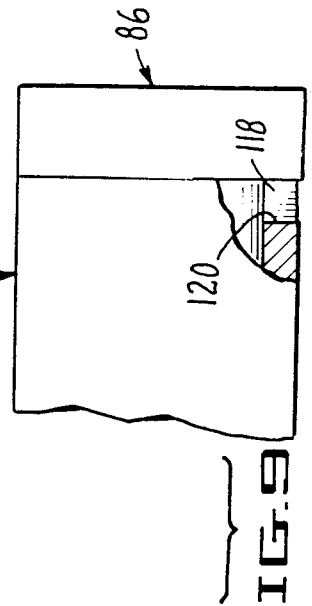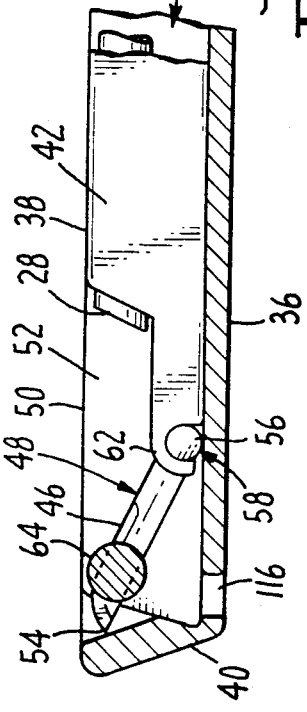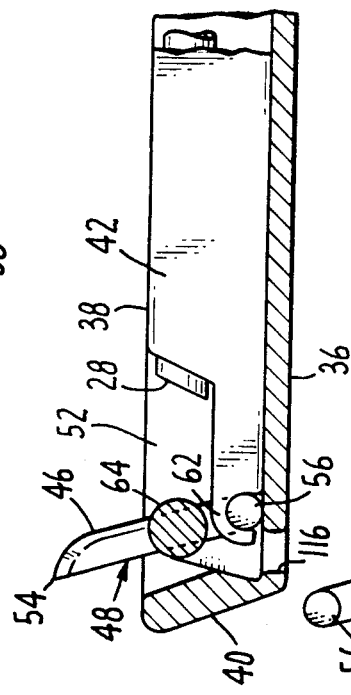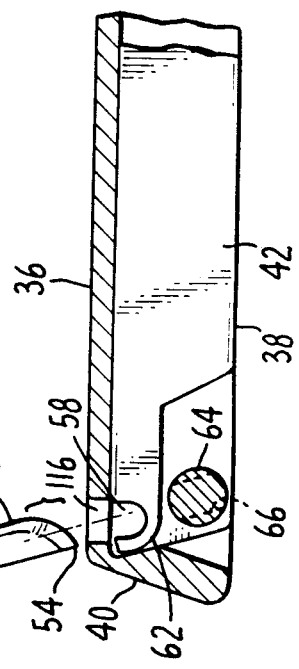

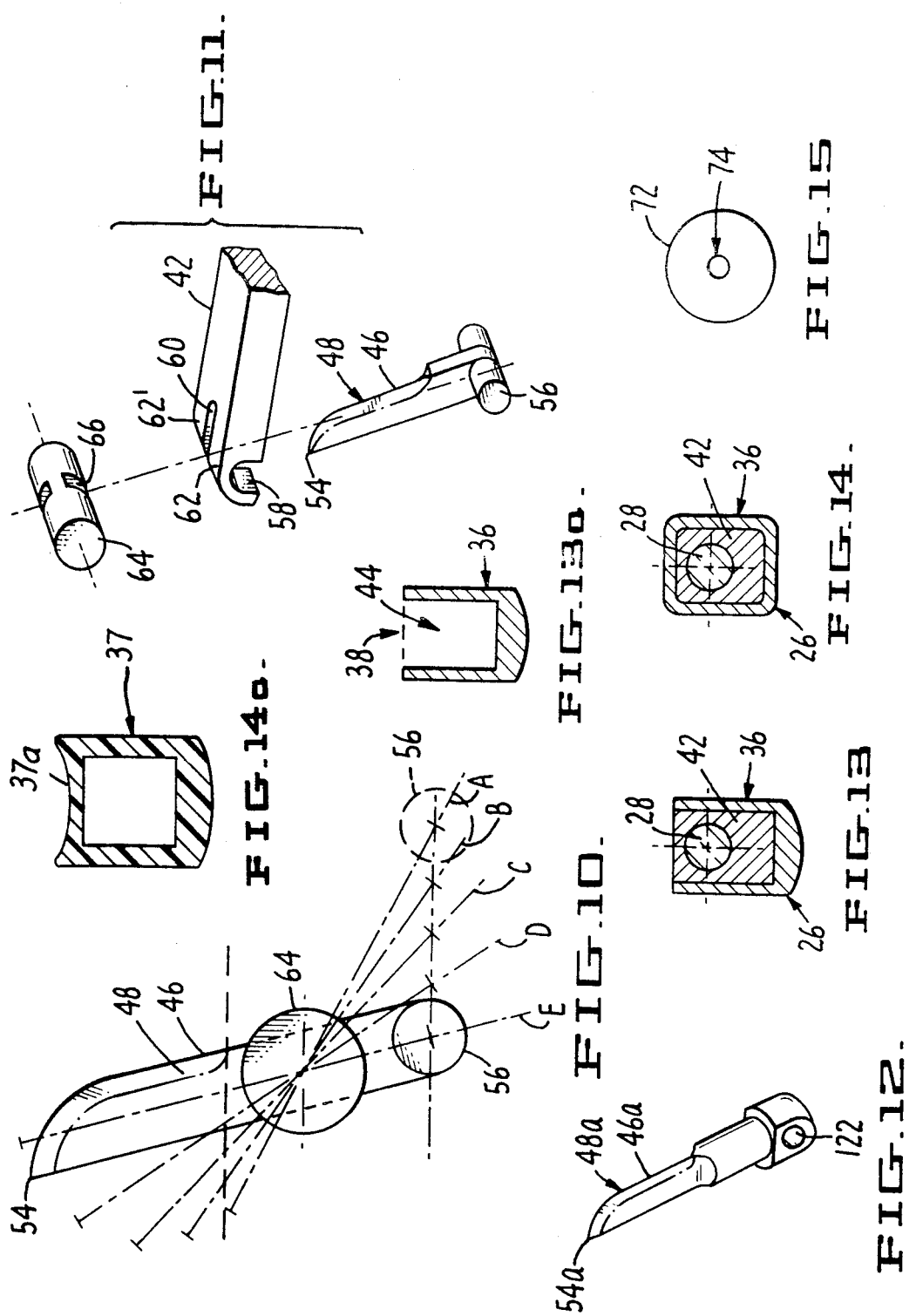

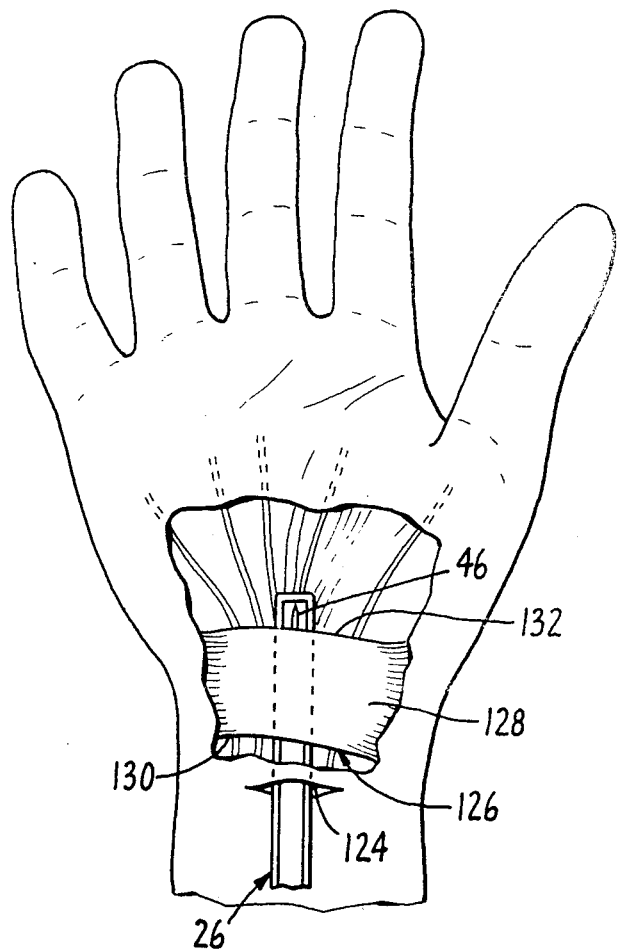
FIG. 17.
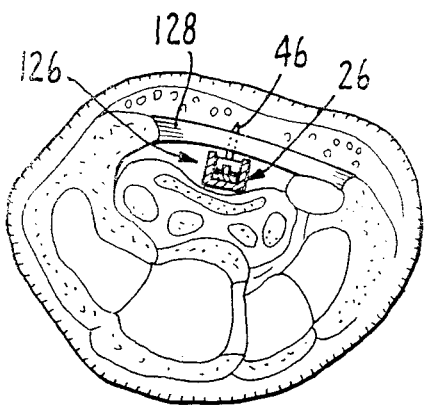
FIG. 16.
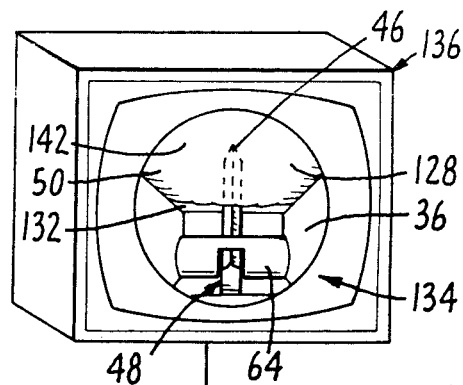
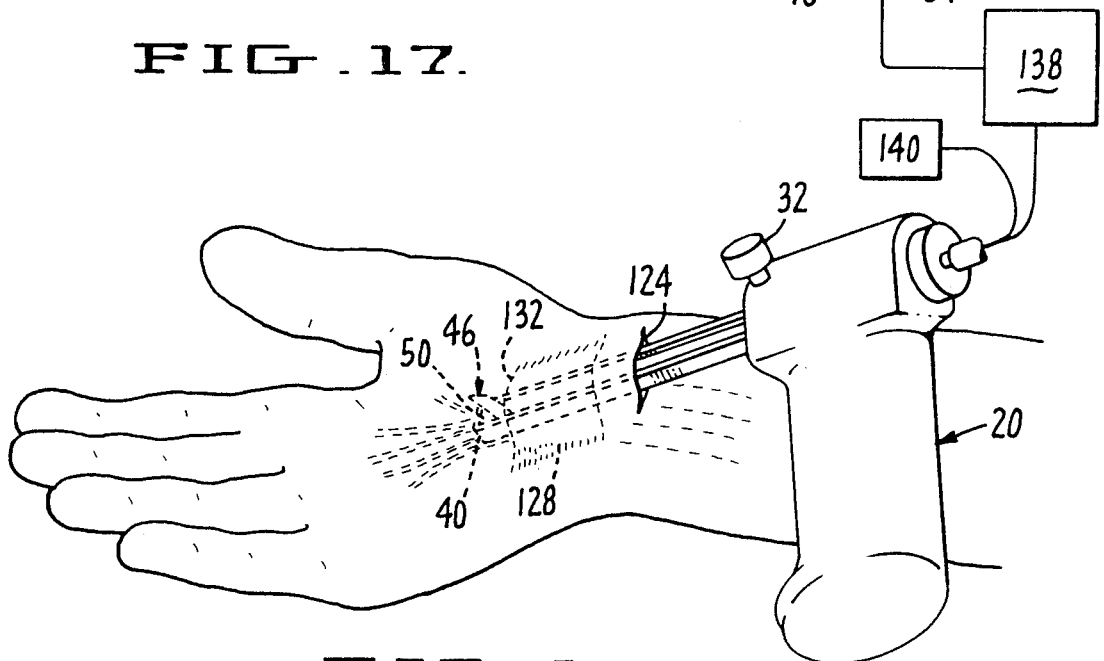
FIG. 18.

SURGICAL INSTRUMENT

This is a continuation of co-pending application Ser. No. 098,610 filed Sept. 18, 1987, abandoned.

Technical Field

The present invention relates generally to a surgical technique utilizing optical device technology and an instrument for performing the technique and, more particularly, to a technique and instrument useful to probe body cavities and manipulate tissue contained therein under continuous observation.

Background of the Invention

Previously, a variety of techniques and apparatus have been used to manipulate tissue in body cavities, generally for the purposes of surgical intervention or biopsy sampling for diagnostic purposes. Generally, the apparatus are designed for particular applications and their configurations are specially arranged for such applications. However, such techniques and apparatus generally suffer from numerous drawbacks.

For example, arthroscopic surgery often requires a number of separate incisions for the insertion of separate devices for expanding the joint, manipulating the tissue, and observing the surgical technique.

In other applications, such as biopsy sampling or surgical manipulation of soft tissue, devices are known which require specialized cutting or sampling surfaces, which often cannot be completely shielded to prevent inadvertent harm to surrounding tissue.

It is therefore considered desirable to provide a surgical method and instrument which provides for the insertion of a single probe into a body cavity and the manipulation of selected tissue under continuous observation. It is also considered desirable to provide a means for shielding the working surface of the instrument, thereby avoiding inadvertent injury to surrounding tissue.

There are other potential applications for which no surgical techniques or apparatus have yet been devised for performing the surgical manipulation within the body cavity. Consequently, the tissue of interest is ordinarily exposed by means of dissection, with the attendant increase in post-operative pain and morbidity. Exemplary of such an application is the surgical technique employed to relieve carpal tunnel syndrome.

The carpal tunnel is formed by an arch of the eight wrist bones, spanned on its palmar surface by the transverse carpal ligament, the flexor retinaculum. The carpal tunnel functions as a large mechanical pulley to provide the appropriate moment arms for the digital flexor tendons as they pass through the tunnel. The tendons can then transmit force out into the fingers and impart only an appropriate amount of tension to develop torque at the level of the wrist.

Within the carpal tunnel, these tendons are lubricated and nourished by two synovial membranes - the radial and the ulnar bursa. The median nerve also shares the carpal tunnel, then branches out to provide sensory innervation to the palmar surfaces of the thumb, index, long and a portion of the ring finger. In addition, a small motor branch of the median nerve supplies the thenar muscles, which are responsible for lifting the thumb into opposition with the fingers.

Carpal tunnel syndrome describes numerous clinical signs and symptoms resulting from pressure on the median nerve inside the carpal tunnel. The typical etiology is increased pressure within the carpal tunnel, which interferes with the function of the median nerve. The patient experiences numbness and tingling in the fingers, together with pain that may radiate as far as the shoulder or base of the neck. Other symptoms include: Impaired grasping ability, due to sensory deprivation from the fingers; Loss of sleep from pain and numbness in the hand; and weakness or atrophy of the thenar muscles.

The pathology generally results from a swelling of the synovial membranes, which is often idiopathic. Carpal tunnel syndrome can also be caused by pressure on the median nerve from rheumatoid arthritis or edema in the final trimester of pregnancy.

Many instances of carpal tunnel syndrome can be treated conservatively, typically with a resting splint and cortisone injection into the carpal tunnel. However, if symptoms persist and/or reoccur, or if the patient has severe sensory deficit or loss of functions in the thenar muscles, then surgical decompression of the nerve by release of the transverse carpal ligament is often indicated.

Currently, surgical decompression is accomplished by a longitudinal incision paralleling the thenar crease. The incision is carried down through the skin, subcutaneous fat, and palmar fascia to divide the palmaris brevis muscle and then the transverse carpal ligament. Although the carpal tunnel is inspected, most cases do not require any surgical treatment within the carpal tunnel, other than the division of the ligament. Thereafter, the skin is sutured and the patient is splinted for approximately three weeks. A typical surgery requires approximately 20–25 minutes, including the dressing, and is performed as an outpatient procedure.

A patient whose occupation does not require extensive use of the hands can generally return to work within a few days, although writing may be difficult if the dominant hand is involved. However, in the frequent cases where the syndrome is occupationally related, i.e., where Workmen's Compensation is involved, the patient is usually disabled for six to eight weeks. If the patient is a manual laborer, two or three months may pass before a return to gainful employment. This post-operative morbidity is primarily due to persistent tenderness in the palm as the scar tissue matures. Most patients experience tenderness in the heel of their hand for four to six months following the surgery.

Previously, a few surgeons would release the carpal tunnel by inserting scissors through a transverse incision proximal to the carpal tunnel. The blind release by division of the ligament would then proceed from the proximal to the distal end. When successful, this technique decompresses the median nerve without scaring the heel of the patient's hand, significantly decreasing postoperative pain and morbidity.

However, transverse incision and blind release is not advisable, due to the risk of incomplete release of the carpal tunnel, or injury to the superficial arterial arch or the median nerve. The superficial palmar arterial arch lies just distal to the distal portion of the carpal ligament. The motor branch of the median nerve, which controls thumb opposition, is typically on the distal radial extent of the carpal tunnel, although anomalies can allow it to penetrate the carpal ligament in any of a number of positions and be subject to injury during blind release procedures.

Thus, it is also considered desirable to provide a surgical method and instrument for carpal tunnel release which reduces postoperative pain and morbidity while minimizing the risk of injury to neural or vascular tissue surrounding the carpal ligament.

Background Art

In addition to the techniques and apparatus previously discussed, additional background for the present invention is included in U.S. Pat. Nos. 3,900,022, 4,137,920, 4,200,111, 4,201,213, 4,275,735, 4,423,727, 4,461,280, 4,474,174, 4,499,899, 4,522,206, 4,539,976, 4,580,563, 4,603,694, 4,620,547 and 4,633,860. Foreign patent documents which also provide background for the invention include German patent documents No. DE 27 37 014, DE 27 48 057 and DE 34 08 243.

Disclosure of the Invention

The present invention provides an improved surgical method for inspecting and manipulating selected tissue in body cavities, while minimizing the risk of injury to surrounding tissue.

In one aspect, the method of the invention employs a surgical instrument comprising a probe having an upper surface and a generally closed distal end, and a lateral aperture on the upper surface and adjacent the distal end. Included in the probe is an optical system disposed at least partially within the probe and having a distal portion positioned adjacent the lateral aperture.

The probe thus provides a viewing space defined generally by the distal portion of the optical system, the distal end of the probe and the lateral aperture, the viewing space being located within the field-of-view of the optical system. Also mounted within the viewing space of the probe is a working tool capable of being extended from the viewing space and through the lateral aperture, outwardly from the probe, and a means for extending the working tool.

In operation, the probe is positioned so that the lateral aperture is adjacent the tissue to be inspected and/or manipulated. The working tool is then extended through the lateral aperture to a position adjacent the selected tissue, allowing the tissue manipulation to be observed.

Another aspect of the invention provides a method of releasing the carpal tunnel by employing the method to divide the flexor retinaculum.

A further aspect of the present invention provides a method for dividing the flexor retinaculum under visual inspection during carpal tunnel release, while minimizing the risk of injury to surrounding tissue. In practicing this method, an incision is made at one end of the carpal tunnel and a probe comprising a cutting blade and an optical system is inserted through the incision and positioned adjacent to the flexor retinaculum. The instrument is then employed to divide the flexor retinaculum, thereby releasing the carpal tunnel, while the optical system enables continuous observation of the portion of the cutting blade within its field-of-view.

A still further aspect of the invention provides a surgical instrument capable of manipulating selected tissue in a body cavity under continuous visual observation, as well as an instrument for dividing the flexor retinaculum under continuous visual observation.

Brief Description of the Drawings

FIG. 1 is an elevational view of an instrument in accordance with the present invention, with certain portions broken away for clarity, and with an optical system and portions of a working tool extension shaft of the probe shown in phantom;

FIG. 2 is a vertical cross-sectional view, partly in elevation and partly in section, of the instrument portrayed in FIG. 1, with the cross-section taken along the line 2—2 in FIG. 1;

FIG. 3 is an exploded fragmentary elevational view, with portions broken away for clarity, showing the outer sheath and the tool extension shaft of the probe of FIG. 1;

FIG. 4 is an enlarged cross-sectional view of the actuator portion of the tool extension shaft of the instrument of FIG. 1;

FIG. 5 is a perspective view of the actuator lever of FIG. 4;

FIG. 6a is a top plan view, with portions broken away, of an outer sheath of the probe of FIG. 1;

FIG. 6b is a bottom plan view of the feature depicted in FIG. 6a;

FIG. 7 is a fragmentary view, with portions in elevation and portions in section, of the outer sheath of the probe of FIG. 1;

FIG. 8 is a view similar to FIG. 7, showing the probe during extension of a cutting blade;

FIG. 9 is a view similar to FIG. 8, in alternate position, showing the replacement of a cutting blade in the probe of FIG. 1;

FIG. 10 is a sectional view of the distal end of the outer sheath of a probe of the present invention, with portions broken away, and with the longitudinal axis of a cutting blade shown in positions respective to the actuation of the working tool extension shaft;

FIG. 11 is an exploded fragmentary view showing the insertion of a cutting blade into the tool pivot and tool extension shaft;

FIG. 12 is a perspective view of an alternative cutting blade in accordance with the present invention;

FIG. 13 is a cross-sectional view of a portion of the surgical instrument of FIG. 1 taken along the lines 13–13;

FIG. 13a is a cross-sectional view of a portion of the surgical instrument of FIG. 3 taken along the lines 13–13a;

FIG. 14 is a view similar to FIG. 13 of an alternative embodiment of the present invention;

FIG. 14a is a cross-sectional view of another embodiment of outer sheath which is useful in the present invention.

FIG. 15 is a elevational-view, from proximal to distal, of the feature displayed in FIG. 3.

FIG. 16 is a cross-sectional view, with portions broken away for clarity, of the probe of the present invention inserted into the carpal tunnel and positioned adjacent the flexor retinaculum;

FIG. 17 is a representation of a wrist, with portions broken away for clarity, and the flexor retinaculum with the probe of FIG. 1 inserted into the carpal tunnel; and FIG. 18 is a diagrammatic view showing a set up of the instrument according to the present invention with certain accessories routinely employed in performing carpal tunnel release.

Modes of Practicing the Invention

This invention provides a novel and improved surgical method and instrument for manipulating selected tissue in body cavities under continuous visual observation, while minimizing the risk of injury to surrounding tissue.

One aspect of the invention provides a surgical instrument for manipulating selected tissue under visual observation. The instrument includes a probe having an upper surface, a generally closed distal end and a lateral aperture on the upper surface adjacent the distal end.

The instrument is provided with the capability for accepting an optical system disposed at least partially within the probe and having a distal portion terminating proximal to the distal end of the probe and adjacent the lateral aperture. The probe thus provides a viewing space defined by the distal portion of the optical system, and the distal end and the lateral aperture of the probe, the space being located within the field-of-view of the optical system.

Also included in the probe is a working tool, located within the viewing space and capable of being extended outward from the viewing space and through the lateral aperture of the probe, together with a means for outwardly extending the working tool.

As an overview, FIGS. 1 through 15 of the drawings illustrate a presently preferred surgical instrument 20 of the present invention, wherein the distal end of each component in a side view is presented to the left unless otherwise noted. As depicted in FIG. 1, instrument 20 includes a grip handle 22, attached to housing 24. The distal end of housing 24 is configured to accept, in rotatable engagement, the proximal portion of probe 26. The structure and function of probe 26 is described in greater detail below.

The proximal end of housing 24 is configured to accept, in releasable telescopic engagement, a sight tube 28 of an optical system 30. However, a specific optical system is not an aspect of the present invention. Numerous conventional optical systems can be employed, such as an examination telescope, more commonly known as an arthroscope, or a miniature video camera.

FIG. 1 also shows locking screw 32, which provides a mechanism to temporarily arrest the rotation of probe 26 within housing 24, thereby allowing the operator to temporarily fix any desired rotational orientation between the grip handle 22 and the probe 26. It will be readily appreciated that the angular orientation between probe 26 and grip handle 22 can also be controlled, e.g., by including a releasably fixed point of articulation between them. Thus, both the rotational and angular orientation between these components of surgical instrument 20 can be controlled by the operator.

In addition, FIG. 1 also depicts trigger 34, located in grip handle 22, which is depressed by the operator to actuate the progressive extension of the working tool from probe 26 and released to permit tool retraction.

A general outline of the main features of probe 26 is presented in greater detail in FIG. 7. In this embodiment, probe 26 includes an outer sheath 36, having an upper surface region 38 and a generally closed distal end 40. As shown in FIG. 14, the upper surface 38 of probe 26 can be provided by outer sheath 36. Alternatively, as shown in FIGS. 13 and 13a, a similar configuration can also be provided by the combined open trough cross-section of the upper surface region 38 of outer sheath 36 and the upper surface of tool extension shaft 42. As used hereafter, reference to the upper surface 38 of probe 26 will include either of these alternatives, unless otherwise indicated.

FIG. 14a is a cross-sectional view of another embodiment of outer sheath 37 which is useful in the present invention. The upper surface 37A of the sheath is slightly concave, as illustrated.

FIG. 7 also depicts a working tool located within the distal end of hollow axial passage 44 of outer sheath 36. The working tool is presented in this embodiment as a cutting blade 46 on blade member 48. The blade member 48 is positioned adjacent to lateral aperture 50, provided in upper surface 38 of outer sheath 36. The distal end of sight tube 28 of the optical system 30 will be positioned proximal to the blade member 48, thereby including the cutting blade 46 of blade member 48 and the lateral aperture 50 within its field-of-view.

The area within the walls of outer sheath 36 bounded by the distal end of sight tube 28 and the probe distal end 40 defines a viewing space 52 which provides a viewing medium for the optical system 30 and a receptacle for the working tool. This field-of-view, extending out from probe 26 through lateral aperture 50, allows continuous observation of the selected tissue in the body cavity as it is manipulated by the working tool.

It will be readily apparent that if the various components of probe 26, such as outer sheath 36, are opaque then the field-of-view of optical system 30 will be limited to viewing space 52 and the surrounding area outside of probe 26 adjacent to lateral aperture 50. However, certain components of probe 26, such as outer sheath 36, can be constructed of transparent materials, such as plastic, thereby substantially broadening the field-of-view of optical system 30 and enabling wider inspection before and during the tissue manipulation.

The outward extension of a working tool in accordance with the present invention is shown in detail in FIGS. 7 through 11. In accordance with one embodiment of the present invention, a blade member 48 has a point 54 and a cutting blade 46. In addition, blade member 48 is fitted with a retaining dowel 56 which is configured to fit within the recess 58 provided in the distal portion of tool extension shaft 42. This shaft 42 also includes a passage 60 (as shown in FIG. 11) configured for accepting and releasably retaining blade member 48 between distal projections 62 and 62'. The distal portion of outer sheath 36 contains axially fixed rotatable tool pivot member 64 having a passage 66 configured to accept blade member 48. As also shown in FIG. 7, the assembly in the distal portion of probe 26 includes blade member 48 releasably retained via dowel 56 between distal projections 62, 62' of shaft 42 and inserted through passage 66 in tool pivot member 64.

With the working tool in retracted configuration, both point 54 and cutting blade 46 of blade member 48 are inside the boundary of upper surface 38 of outer sheath 36. As depicted in FIG. 8, when tool extension shaft 42 is moved longitudinally, blade member 48 moves through passage 60 in rotatable pivot member 64. As shown in further detail in FIG. 10, the distal longitudinal displacement of tool extension shaft 42 causes a corresponding displacement of blade dowel 56. This displacement moves blade member 48 further through passage 60, causing a rotation of tool pivot member 64 and a concomitant outward extension of blade point 54.

As shown in FIG. 10, a change in the relative distance between longitudinally displaceable blade dowel 56 and axially fixed, rotatable pivot member 64 changes the angle between the longitudinal axis of blade member 48 and the longitudinal axis of probe 26. Thus, the moment arm of blade member 48 through pivot member 64 decreases as the distal portion of tool extension shaft 42 approaches pivot member 64. It will be apparent from FIG. 10 that during tool extension each successive increment of longitudinal displacement of tool extension shaft 42 produces a greater increment in angular displacement of blade member 48, as shaft 42 approaches pivot member 64. In this manner a relatively long working tool can be extended outward from probe 26 by rotating through an arc into a fully extended position.

The cooperative action of tool extension shaft 42 and pivot member 64 thus produces the outward extension of blade member 48 toward the lateral aperture 50 of outer sheath 36. At a certain blade angle, indicated as angle B in FIG. 10, the point 54 and cutting blade 46 of blade member 48 project through lateral aperture 50 and above the boundary of upper surface 38 of probe 26. In this manner, the assembly provides a mechanism to extend the working tool of the probe 26 toward selected tissue positioned adjacent to the probe. When desired, the working tool can be retracted and fully enclosed within the probe, to avoid inadvertent injury to tissue surrounding the selected tissue.

As shown in FIG. 3, the remaining components which provide the mechanism of probe 26 include probe retainer 66, configured as a hollow cylinder with a retaining ring 68 and an annular groove 70. This groove 70 accepts the extension portion of locking screw 32 (FIG. 1) which, when engaged, arrests the rotation of probe retainer 66 within housing 24.

As can also be seen from FIG. 3, outer sheath 36 provides a longitudinally extended axial passage 44 (shown more clearly in cross-section in FIG. 13a) which accepts tool extension shaft 42 of working tool actuator 72. As discussed below, axial passage 44 also accommodates the sight tube portion of optical system 30, as sight tube 28 will be telescopically engaged with working tool actuator 72 by insertion into sight tube passage 74 provided therein.

From the above description, it will be readily apparent that probe 26 can also be provided as a replaceable and/or disposable component of surgical instrument 20. This configuration provides the ability for the rapid exchange of the working tool of the instrument or, for example, replacement of blade member 48, without resorting to additional implements such as screw drivers or wrenches.

The components of an apparatus which provide a mechanism for extension of the working tool are also displayed in FIG. 3. The components are assembled in a sleeve 76, having an annular ridge 78 and a slot 80, provided to receive the actuating lever 82, as shown in FIGS. 4 and 5.

Referring again to FIG. 3, working tool actuator 72 includes tool extension shaft 42, a cylindrical barrel portion 84 and a stop portion 86. To facilitate insertion into the passage 88 provided in probe retainer 66, working tool actuator 72 is configured so that tool extension shaft 42 telescopically engages with probe outer sheath 36 via axial passage 44.

When working tool actuator 72 and outer sheath 36 are assembled, as shown in FIG. 2, it will be desirable to include spring 90 and spring follower 92 in sleeve recess 94, so that they contact annular ridge 78 as a spring stop. This assembly provides a mechanism for the automatic retraction of the working tool when trigger 34 is released.

As depicted in FIG. 3, the distal portion of sleeve 76 is configured to accept collar 96 into a second sleeve recess 98. This collar is designed to telescopically engage with barrel portion 84 of working tool actuator 72 and releasably retain the actuator by the operation of set screw 100. When assembled, the working tool actuator 72 and collar 96 are rotatably engaged within sleeve 76.

Outer sheath 36 is then engaged with tool extension shaft 42 by inserting the cylindrical portion of probe retainer 66 into sleeve recess 98, whereby axial passage 44 is telescopically engaged around tool extension shaft 42. Thereafter, locking screw 32 engages with annular groove 70 in probe retainer 66 and the ring 68 of probe retainer 66 rests against sleeve 76.

As can be seen in FIG. 2, when operating the instrument 20, the rotational orientation between lateral aperture 50 of probe 26 and grip handle 22 can be set to any desired position by releasing locking screw 32 and rotating probe retainer 66 within sleeve recess 98. This allows the operator to assume a comfortable position relative to the patient, and provide appropriate positioning of the lateral aperture 50 adjacent the selected tissue. As discussed previously, it will also be appreciated that the angular orientation between probe 26 and grip handle 22 can be controlled by including a releasably fixed point of articulation between them. Thus the orientation between these components of surgical instrument 20 can be controlled in three dimensions.

As seen in greater detail in FIGS. 2 and 4, the grip handle 22 includes a trigger 34 which, when moved, displaces actuating lever 82 fitted into lever pivot member 102 and retained by second set screw 104. As will be readily understood, the displacement of actuating lever 82, fitted through slot 80 in sleeve 76, causes an inverse displacement of lever engagement portion 106. In the assembled instrument, engagement portion 106 engages with a second annular groove 108 in collar 96 in order to actuate tool extension shaft 42. During operation of the surgical instrument, trigger movement is constrained to a single axis by the cylindrical extension 110, whose outer surface 112 telescopically engages with recess 114 in grip handle 22.

Also shown in FIGS. 7 and 8 is the distal portion of the sight tube 28 of optical system 30. As disclosed above, the optical system employed in the present invention can be a conventional fibre optics device, sometimes known generically as a Hopkins rod-lens telescope, an examination telescope or an arthroscope. This device includes an elongated sight tube portion 28 for housing optical fibers. At the proximal end of the optical system will generally be an eye piece and an attachment for a light source (not shown) to convey light via a fibre optic bundle to the field-of-view of the system. Thus, at the distal end of the sight tube 28, the optical system 30 will be configured to both project light and return a visual image of the field-of-view along a separate optical path.

After insertion of the sight tube 28 into passage 74 of working tool actuator 72 (shown in FIG. 15) the distal portion of the sight tube 28 will be positioned proximally to the working tool, e.g. blade member 48 and the distal end 40 of probe 26. The field-of-view of the optical system 30 will then include the viewing space 52 defined as above described. In addition, the optical system field-of-view will extend through the lateral aperture 50 provided in the upper surface 38 of outer sheath 36, in order to include the extended working tool and the selected tissue to be manipulated.

In the conventional operation of such an optical system, the image will be directed to an eye piece for the surgeon, and optionally to a camera for recording the visual images. However, as shown in FIG. 18, it will generally be preferred to include a video camera in the optical system and broadcast these images in real time to a display monitor, thereby enabling the surgeon to observe the field-of-view during probe positioning and tissue manipulation.

While this continuous observation can be accomplished using such conventional examination telescopes, it may be considered desirable to include a portion of the video camera's electronic components within the instrument 20 or the probe 26. For example, a miniature video camera can be located at the same approximate position as the distal portion of sight tube 28 in FIG. 7. The images recorded by the camera could then be transmitted to a monitor for observation.

In the preferred embodiments of instrument 20, distal end 40 of probe 26 is configured so as to displace any tissue it contacts during insertion into the body cavity, while minimizing the potential for tissue injury. In one aspect, the distal end 40 is shaped with a taper tending away from the lateral aperture 50 and the upper surface 38 of probe 26. Thus, the distal end 40 of probe 26 forms an inclined plane having an acute angle with upper surface 38, as depicted most clearly in FIGS. 7 through 9. This shape will tend to divert any displaceable tissue away from the upper surface 38 and lateral aperture 50 while probe 26 is moved distally.

It is also considered desirable to configure upper surface 38 of probe 26 as a flat or concave surface which closely corresponds to the surface of the selected tissue, thereby reducing the potential for any tissue adjacent to the lateral aperture 50 to project into viewing space 52. For example, as shown in FIG. 16, the upper surface 38 of probe 26 can be configured to approximate the lower surface of the flexor retinaculum, thereby excluding any displaceable tissues, such as the median nerve or the digital flexor tendons, from the region around the lateral aperture 50. However, it will be readily apparent that even a probe 26 having a convex upper surface 38 will provide generally the same benefits, so long as the radius of curvature is substantially complementary to the surface of the tissue to be manipulated.

In addition, the outer sheath 36 which forms a portion of the boundary of viewing space 52 will also exclude mobile tissues such as nerve(s), tendons, blood vessels and their associated tissues (synovial membrane) and prevent their inadvertent contact with the working tool while it is in a retracted position.

As an additional or alternative means of excluding tissue from the lateral aperture 50 or viewing space 52, upper surface 38 of outer sheath 36 can be provided with a displaceable cover which substantially seals lateral aperture 50 until the working tool is extended. Such a cover may be provided, for example, by a thin film of transparent plastic which would be divided or displaced by the extension of blade member 48. Such a temporary cover would also facilitate the maintenance of a sterile field within the viewing space 52, prior to use of instrument 20.

As shown in FIGS. 6a and 6b, there is desirably also provided in outer sheath 36 a second lateral opening 116 located approximately diametrically opposite lateral aperture 50. As shown in FIG. 9, lateral opening 116 facilitates the insertion and removal of a working tool, such as blade member 48, from probe 26, for example to replace a dull blade or to substitute a different working tool.

In order to prevent accidental loss or displacement of the working tool while the instrument is in use, stop portion 86 of working tool actuator 72 is also provided with detent 118. In most rotational orientations of grip handle 22 to probe 26, detent 118 will contact the proximal surface of sleeve 76 or housing 24 before recess 58 of tool extension shaft 42 aligns with opening 116. However, sleeve 76 is also provided with reciprocal recess 120 (as shown more clearly in FIG. 9). Comparing FIGS. 7 and 9 demonstrates that, when the working tool actuator 72 and probe 26 are rotated within sleeve 76 to a certain position, detent 118 can engage with reciprocal recess 120. This allows recess 58 and tool dowel 56 to move to a position adjacent opening 116 and thus facilitate the blade removal depicted in FIG. 9. This feature of instrument 20 also permits the exchange or replacement of a working tool without resort to additional implements.

One alternative embodiment for a working tool of the present invention is demonstrated by the blade member 48a of FIG. 12. This working tool has blade point 54a and cutting blade 46a in common with blade member 48. However, blade member 48a provides an alternative engagement mechanism to a tool extension shaft. Blade member 48a includes passageway 122 configured to accept an engagement rod from the distal portion of an tool extension shaft 42a (not shown). As shown in FIG. 14, this alternative working tool embodiment might include a slight modifications to the cross-section of tool extension shaft 42a and outer sheath 36a (also not shown). However, the essential principles of the operation remain the same.

The various components of surgical instrument 20 are generally formed from metals usually employed in known surgical instruments. It is anticipated, however, that any material suitable for the uses intended may be used without departing from the teachings of the present invention. For example, as disclosed previously, various components of surgical instrument 20 can be constructed of plastic, either opaque or transparent, thereby providing benefits such as an expanded field-of-view and greater economy with interchangeable probes. Likewise, the locking mechanisms, such as setscrews 100 and 104 are well known in the art and may be modified to accommodate various structures consistent with the present invention.

Also in accordance with the present invention, the method and surgical instrument may be used to manipulate selected tissue, particularly tissue located in a body cavity. In one aspect, therefore, the invention provides a surgical method for manipulating selected tissue in a body cavity under visual observation, while minimizing the risk of injury to surrounding tissue.

One embodiment of the method comprises employing a surgical instrument comprising a probe having an upper surface, a generally closed distal end and a lateral aperture on the upper surface adjacent the closed distal end. In use, the instrument will include an optical system disposed at least partially within the probe and having a distal portion terminating adjacent the lateral aperture of the probe.

Located within the probe is a viewing space, defined by the distal portion of the optical system, and the distal end and the lateral aperture of the probe, the space being located within the field-of-view of the optical system.

Also included in the probe is a working tool capable of being extended outwardly from the defined space and through the lateral aperture of the probe, and a means for radially extending the tool.

The probe is positioned so that the lateral aperture is adjacent the tissue to be manipulated. The working tool is then extended outward through the lateral aperture to a position deemed appropriate to manipulate the tissue. In the event the tool extension alone does not effect the desired manipulations, the probe is then maneuvered along the desired path, thereby manipulating the tissue.

In FIGS. 16 through 18 and the explanation which follows, particular reference is made to dividing the transverse carpal ligament (flexor retinaculum) in order to decompress the median nerve in the carpal tunnel. However, it will be readily appreciated that the principles and operations of the present invention may be widely adapted to perform tissue manipulations on any selected tissue, by employing a variety of working tools. The benefits of the invention will be particularly manifest during the manipulation of tissue located within a cavity in the body, thereby avoiding the risks which accompany blind surgery.

In the prior art, the procedure for blind release of the flexor retinaculum involved grave risk of complications through inadvertent damage to surrounding neural and vascular tissue located within, and adjacent to, the carpal tunnel. By use of the present invention, carpal tunnel release can be accomplished under visual inspection and the surgeon can avoid damage to structures within the carpal tunnel and vascular and neural tissue beyond, while minimizing post-operative pain and morbidity.

In operation, as shown in FIG. 17, the preferred embodiment of the present method applied to carpal tunnel release is accomplished by forming a short transverse or oblique incision 124 located proximal to the carpal tunnel 126 and the wrist flexion crease (not shown). After longitudinal spreading dissection, to avoid injury to the sensory nerves, the incision 124 is continued through the deep fascia of the forearm, the distal extension of which leads to the flexor retinaculum 128. After an incision through the finger flexor synovium (not shown), extension of the wrist will then expose the proximal opening of the carpal tunnel 130, thereby forming a passage to the carpal tunnel 126.

After adjusting the instrument 20 to accommodate a comfortable working position for the surgeon, e.g., controlling the orientation between probe 26 and grip handle 22 via locking screw 32, the probe 26 is inserted through incision 124 and desirably through the length of the carpal tunnel 126 to the distal edge 132 of the flexor retinaculum 128.

As shown in FIG. 18, by employing the optical system 30, and through manipulation of the patient's extremities, the anatomy within the carpal tunnel 126 can be clearly visualized on the display 134 of video monitor 136 and the structures defined, and the distal edge 132 of the flexor retinaculum 128 can be located. The image conveyed to monitor 136 by video camera 138 can be enhanced by light source 140.

As noted previously and depicted in FIG. 16, the distal end 40 of probe 26 will desirably have gently displaced the tendons, bursa (synovial membrane) and median nerve found within the carpal tunnel 126, to facilitate insertion of the probe. Then, the lateral aperture 50 of probe 26 will be positioned adjacent the medial surface 142 of the flexor retinaculum 128 and, desirably, the configuration of probe upper surface 38 will exclude the displaced tissues (shown generally in FIG. 16 as the structures immediately below probe 26) from the region surrounding the lateral aperture.

FIG. 18 shows that, at the appropriate location, blade member 48 will be extended to enable cutting blade 46 to contact the distal edge 132 of the flexor retinaculum 128, while the surgeon views the tissue to be divided via the display 134 of optical system 30. The blade point 54 will desirably be extended to a position sufficient to completely release the ligament, as can be seen most clearly in FIG. 16. It is desirable to avoid excess extension of the blade member 48 and blade point 54, in order to avoid injury to the soft tissues superficial to the flexor retinaculum.

FIG. 18 also shows that, while viewing through lateral aperture 50 the intended path of the extended cutting blade 46, probe 26 is then withdrawn, thereby dividing the flexor retinaculum 128 and releasing the carpal tunnel 126. In the event of incomplete division, the steps described above can be repeated with greater elevation of cutting blade 46, or taking advantage of the increased blade penetration due to the tissue displacement from the incision first made.

As can be seen from the above description, the present invention provides a novel and improved surgical method for dividing selected tissue while minimizing the risk of injury to surrounding tissue. In a particular application, the present invention allows the insertion of the instrument into the carpal tunnel cavity through a transverse incision and release of the tunnel with minimal post-operative pain and morbidity, and minimal risk of complications.

Although the invention has been described with particular reference to specific procedural sequences, it is obvious that many modifications can be made without departing from the spirit and scope of the present invention. By way of example, the carpal tunnel release could be performed by dividing the tissue from the proximal to the distal end of the flexor retinaculum, simply by reversing the orientation of blade member 48 so that cutting blade 46 faces distally. However, this procedure is considered less preferred because, while the procedure would be safer with the instrument of the present invention, the attendant risks would be higher than with the preferred method. Also, there would be a tendency for the operator to overshoot during manipulation of the instrument, once the resistance to the movement of probe 26 is decreased by the complete division of the ligament.

In addition, while the invention is described in some detail with reference to dividing the flexor retinaculum to effect release of the carpal tunnel, it will be apparent that similar procedures can be employed to divide other tissue, particularly ligamentous tissue.

Furthermore, although the invention has been described with particular reference to specific structural configurations, it is obvious that many modifications can be made without departing from the spirit and scope of this aspect of the present invention. By way of example, the handle of the instrument is merely one of many alternative configurations.

In addition, the optical system 30 can be configured to include various elements of the actuating system and thus incorporate both functions.

Obviously, many other modifications and variations of the present invention are possible after consideration of the present disclosure. It is therefore to be understood that within the scope of the appended claims, the invention may be practiced otherwise than as is specifically described.

We claim:

1. A surgical instrument for manipulating selected tissue in a body cavity under visual inspection, comprising:
   (a) a probe having an upper surface, a generally closed distal end, and a lateral aperture in said upper surface and adjacent said closed distal end; wherein the upper surface adjacent to the lateral aperture is configured generally as a flat or concave surface; wherein said distal end slopes away from said upper surface in a manner such that said distal end diverts displaceable tissue it contacts away from the region of the lateral aperture and said upper surface;
   (b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;
   (c) a working tool mounted within the viewing space and capable of being extended from the viewing space and through the lateral aperture; and
   (d) means for extending the working tool outwardly from the viewing space and through the lateral aperture;
   (e) a grip handle rotatably connected to said probe; and
   (f) adjustment means for adjusting the rotational orientation between said lateral aperture of said probe and said grip handle; wherein said adjustment means is adapted to temporarily fix said rotational orientation.

2. An instrument as recited in claim 1, wherein the grip handle comprises actuator means for extending the working tool through the lateral aperture of the probe.

3. An instrument as recited in claim 2, wherein the instrument further comprises means for automatically retracting the working tool upon release of the actuating means.

4. An instrument as recited in claim 1 wherein the distal end is configured generally as an inclined plane which forms an acute angle with the upper surface of the probe.

5. An instrument as recited in claim 1, said probe further comprising means for exchanging or replacing the working tool of the probe without requiring additional implements.

6. An instrument as recited in claim 1, wherein the working tool comprises a cutting blade capable of dividing the selected tissue.

7. An instrument as recited in claim 1, wherein means for accepting an optical system accommodates a conventional examination telescope.

8. An instrument as recited in claim 1, wherein the means for extending the working tool through the viewing space and the lateral aperture of the probe comprises a longitudinally displaceable actuation shaft contained within the probe, said actuation shaft being connected to said working tool in actuating relationship therewith providing means for transforming longitudinal displacement of the actuation shaft into outward extension of the working tool.

9. An instrument as recited in claim 8, wherein said actuation shaft is adapted to respond to actuating movement by an operator of the instrument; and wherein each additional increment of longitudinal displacement of the actuation shaft produces a correspondingly greater increment in the extension of the working tool.

10. An instrument as recited in claim 9, wherein the working tool is cooperatively engaged with an axially fixed, rotatable pivot in the distal end of the probe so that longitudinal displacement of the actuation shaft produces an angular displacement of the working tool as the actuation shaft approaches the pivot, thereby outwardly extending the working tool.

11. An instrument in accordance with claim 1, wherein said probe is detachably connected to said grip handle and is disposable.

12. An instrument in accordance with claim 1, wherein said probe includes a flat upper surface, parallel sides, and a convex lower surface.

13. A surgical instrument for dividing the flexor retinaculum under visual inspection during carpal tunnel release, while minimizing the risk of injury to surrounding tissue, comprising:
   (a) a probe having an upper surface, a generally closed distal end, and a lateral aperture in said upper surface and adjacent said closed distal end; wherein said distal end slopes away from said upper surface in a manner such that said distal end diverts displaceable tissue it contacts away from the region of the lateral aperture and said upper surface; wherein said upper surface of said probe adjacent to said lateral aperture is configured generally as a flat or concave surface;
   (b) means for accepting an optical system disposed at least partially within the probe, said system having a distal portion terminating adjacent the lateral aperture, thereby defining a viewing space between the distal portion of the optical system, and the distal end and the lateral aperture, said viewing space located within the field-of-view of the optical system;
   (c) a cutting blade mounted within the viewing space and capable of being extended from the viewing space and through the lateral aperture;
   (d) means for extending the working tool outwardly from the viewing space and through the lateral aperture;
   (e) a grip handle rotatably connected to said probe; wherein said handle includes actuator means for extending said cutting blade through said lateral aperture;
   (f) adjustment means for adjusting the rotational orientation between said lateral aperture of said probe and said grip handle; wherein said adjustment means is adapted to temporarily fix said rotational orientation; and
   (g) retraction means for automatically retracting said cutting blade upon release of said actuator means.

14. An instrument as recited in claim 13 wherein the probe is configured to be inserted into the carpal tunnel before the flexor retinaculum is divided.

15. An instrument as recited in claim 13, wherein the distal end is configured generally as an inclined plane which forms an acute angle with the upper surface of the probe.

16. An instrument as recited in claim 13, said probe further comprising means for exchanging or replacing the cutting blade of the probe without requiring additional implements.

17. An instrument as recited in claim 13, wherein the means for accepting an optical system accommodates a conventional examination telescope.

18. An instrument as recited in claim 13, wherein the means for extending the cutting blade through the viewing space and the lateral aperture of the probe comprises a longitudinally displaceable actuation shaft contained within the probe, said actuation shaft being connected to said cutting blade in actuating relationship therewith providing means for transforming longitudinal displacement of the actuation shaft into outward extension of the cutting blade; wherein said actuation shaft is adapted to respond to movement of said actuator means.

19. An instrument as recited in claim 18 wherein each additional increment of longitudinal displacement of the actuation shaft produces a correspondingly greater increment in the extension of the cutting blade.

20. An instrument as recited in claim 19 wherein the cutting blade is cooperatively engaged with pivot means in the distal end of the probe so that longitudinal displacement of the actuation shaft produces an angular displacement of the cutting blade as the actuation shaft approaches the pivot means, thereby outwardly extending the cutting blade.

21. An instrument in accordance with claim 18, wherein said probe is detachably connected to said grip handle; wherein said upper surface adjacent to said lateral aperture is flat; and wherein said actuation shaft is adapted to respond to actuating movement of a trigger carried by said grip handle.

22. An instrument in accordance with claim 13, wherein said probe is detachably connected to said grip handle and is disposable.

23. An instrument in accordance with claim 13, wherein said probe includes a flat upper surface, parallel sides, and a convex lower surface.

* * * * *